United States Patent [19]

Moore et al.

[11] Patent Number: 5,420,359
[45] Date of Patent: May 30, 1995

[54] CHLOROFLUOROETHER COMPOSITIONS AND PREPARATION THEREOF

[75] Inventors: George G. I. Moore, Afton; Richard M. Flynn, Mahtomedi, both of Minn.; Robert J. Kaufman; Thomas J. Richard, both of University City, Mo.

[73] Assignees: Minnesota Mining and Manufacturing Company, St. Paul, Minn.; HemaGen/PFC, St. Louis, Mo.

[21] Appl. No.: 132,787

[22] Filed: Oct. 7, 1993

Related U.S. Application Data

[63] Continuation of Ser. No. 990,786, Dec. 11, 1992, abandoned.

[51] Int. Cl.$^6$ ............................................. C07C 43/12
[52] U.S. Cl. ........................................ 568/684; 568/669; 568/615; 568/632; 568/649; 568/662; 568/663
[58] Field of Search ............... 568/615, 684, 669, 632, 568/649, 662, 663

[56] References Cited

U.S. PATENT DOCUMENTS

| | | | |
|---|---|---|---|
| 3,435,078 | 3/1969 | Nychka et al. | |
| 3,739,033 | 6/1973 | Anello et al. | 260/615 F |
| 3,778,381 | 12/1973 | Rosano et al. | |
| 3,911,138 | 10/1975 | Clark, Jr. | 424/352 |
| 4,104,314 | 8/1978 | Terrell | 260/614 |
| 4,289,499 | 9/1981 | Clark, Jr. et al. | 23/230 B |
| 4,337,211 | 6/1982 | Ezzell et al. | 260/456 F |
| 4,452,818 | 6/1984 | Haidt | 424/352 |
| 4,510,335 | 4/1985 | Lagow et al. | 568/683 |
| 4,686,024 | 8/1987 | Scherer, Jr. et al. | 204/157.95 |
| 4,755,567 | 7/1988 | Bierschenk et al. | 525/409 |
| 4,808,651 | 2/1989 | Blickle et al. | 524/366 |
| 4,815,446 | 3/1989 | McIntosh | 600/3 |
| 4,859,747 | 8/1989 | Bierschenk et al. | 525/409 |
| 4,895,876 | 1/1990 | Schweighardt et al. | 514/747 |
| 5,053,536 | 10/1991 | Bierschenk et al. | 562/582 |
| 5,077,036 | 12/1991 | Long, Jr. | 424/5 |
| 5,093,432 | 3/1992 | Bierschenk et al. | 525/331.6 |
| 5,114,703 | 5/1992 | Wolf et al. | 424/5 |
| 5,116,599 | 5/1992 | Rogers, Jr. et al. | 424/9 |

FOREIGN PATENT DOCUMENTS

| | | | |
|---|---|---|---|
| 0190393 | 8/1986 | European Pat. Off. | |
| 0295582 | 12/1988 | European Pat. Off. | |
| 0440925A1 | 8/1991 | European Pat. Off. | A01N 1/02 |
| 2315928 | 1/1973 | Germany | C07C 43/12 |
| 2319971 | 11/1973 | Germany | |
| WO89/10118 | 11/1989 | WIPO | A61K 31/02 |
| WO90/03357 | 4/1990 | WIPO | C07C 43/12 |
| WO9003409 | 4/1990 | WIPO | |
| WO90/06296 | 6/1990 | WIPO | C07B 39/00 |
| 9311868 | 6/1993 | WIPO | |

OTHER PUBLICATIONS

Journal of Organic Chemistry, vol. 56, No. 22, 25 Oct. 1991, Easton US, pp. 6348–6351, Chang-Ming Hu et al, "Redox-Initiated Per(poly)fluoroalkylation of Olefins by Per(poly)Fluoroalkyl Chlorides", see p. 6350, col. 1 penultimate paragraph.

Journal of Organic Chemistry, vol. 35, No. 11, Nov. 1970, Easton US, pp. 3730–3733, L. R. Anderson et al, "Perhaloakyl Hypochlorites and Pentafluorosulfur Hypochlorite".

(List continued on next page.)

*Primary Examiner*—Howard T. Mars
*Assistant Examiner*—Michael B. Hydorn
*Attorney, Agent, or Firm*—Wood, Herron & Evans

[57] ABSTRACT

Normally liquid chlorofluoroether compositions consisting or consisting essentially of one or a selected mixture of perhalogenated chlorofluoroether compounds are provided by direct fluorination of the corresponding chloroether or chlorofluoroether precursors. The compositions are useful, for example, as heat transfer agents, blood substitutes, and solvents.

5 Claims, No Drawings

OTHER PUBLICATIONS

"Chemical Abstracts Eleventh Collective Index, Chemical Substances", American Chemical Society, see p. 32172CS, col. 1: Hexane, 1-chloro-1,1,2,2,3,3,4,4,5,5,6,6.

Adcock, J. L. and W. D. Evans, J. Org. Chem. 1984, 49, 2719-23.

Banks, R. E., *Preparation, Properties, and Industrial Applications of Organofluorine Compounds*, pp. 93-95, John Wiley & Sons, New York (1982).

Hudlicky, M., *Chemistry of Organic Fluorine Compounds*, Second Edition, pp. 225-226, Ellis Horwood, New York (1992).

Lowe, K. C., "Perfluorochemicals in Medicine", *Chem. Ind.*, Feb. 4, 1991, pp. 83-88.

K. Yamanouchi and C. Heldebrant, "Perfluorochemicals as a blood substitute," Chemtech, Jun. 1992, pp. 354-359.

CHLOROFLUOROETHER COMPOSITIONS AND PREPARATION THEREOF

This is a continuation of application Ser. No. 07/990,786 filed Dec. 11, 1992, now abandoned.

This invention relates to chlorofluoroether compositions. In another aspect, this invention relates to a process for the preparation of chlorofluoroether compositions by direct fluorination of fluorinatable chloroether or chlorofluoroether precursors.

Highly fluorinated organic compounds or fluorochemicals (for example, perfluorochemicals such as perfluoroalkanes, perfluoroethers, and perfluoroalkyl tertiary amines) are known to be essentially chemically and pharmaceutically inert. This inertness makes such compounds suitable for numerous industrial uses, e.g., as heat transfer agents. Many of such compounds (and emulsions and dispersions thereof) are also capable of dissolving, transporting, and delivering biologically and chemically significant quantities of oxygen, rendering such compounds useful as "blood substitutes," which can be employed in the treatment of heart attack, stroke, and other vascular obstructions, and as adjuvants to coronary angioplasty, cancer radiation treatment, and chemotherapy.

In addition to inertness, fluorochemical purity is also desirable and important for many uses such as biomedical applications and electronic testing, and purity varies according to the preparative method utilized. Substitution methods of preparation (e.g., electrochemical fluorination), which involve replacement of the hydrogen atoms in a hydrocarbon analogue with fluorine, are often employed. Such methods, however, are somewhat "unselective" and can produce mixtures of unpredictable composition due to incomplete fluorination, cleavage, and rearrangement. Fluorochemicals of greater purity can be obtained by oligomerization techniques, but oligomerization is limited by the availability of suitable fluorinated starting compounds. (See K. C. Lowe, "Perfluorochemicals in Medicine" *Chem. Ind.*, Feb. 4, 1991, pages 83–88, and R. E. Banks, *Preparation, Properties, and Industrial Applications of Organofluorine Compounds*, pages 93–95, John Wiley & sons, New York (1982).)

Numerous fluorochemicals of different molecular structures (and prepared by different techniques) have been developed, but the search for new fluorochemicals with improved properties continues.

U.S. Pat. No. 4,510,335 (Lagow et al.) describes perfluorinated branched ether compounds useful as synthetic blood substitutes and perfusion media.

U.S. Pat. No. 4,686,024 (Scherer et al.) discloses fluorochemicals including secondary chlorine-containing, cyclic perhalogenated chlorofluoroethers and chlorofluoroalkanes and asserts that chlorine-containing perfluoro chemicals have desirable properties as oxygen-carrying fluids.

U.S. Pat. No. 5,053,536 (Bierschenk et al.), as well as International Patent Publication Nos. WO 90/03409 (Exfluor Research Corporation) and WO 90/03357 (Exfluor Research Corporation and 3M Corporation), describe perfluoropolyethers and perhalogenated chlorofluoropolyethers prepared by direct fluorination. The compositions of WO 90/03409 contain a plurality of molecular species with a range of molecular weights, rather than a single molecular species of discrete molecular weight.

U.S. Pat. Nos. 3,739,033 (Anello et al.), U.S. Pat. No. 4,104,314 (Terrell), and U.S. Pat. No. 4,337,211 (Ezzell et al.) describe novel chlorofluoroethers.

Briefly, in one aspect, this invention provides a normally liquid chlorofluoroether composition which consists or consists essentially of a perhalogenated chlorofluoroether compound having at least 5 carbon atoms, from 1 to 5 ether oxygen atoms, and at least one chlorine atom, the ether oxygen atoms being separated by at least 2 catenary carbon atoms and the chlorine atoms being bonded to primary carbon atoms (i.e., —$CF_2Cl$). Thus, the composition consists or consists essentially of one perhalogenated chlorofluoroether compound as the single molecular species in the composition. If a "selected mixture," i.e., a predetermined mixture of selected compounds, is desired for a particular use, the composition can consist or consist essentially of a mixture of two or more of the perhalogenated chlorofluoroether compounds of discrete, non-random molecular weights, the selected perhalogenated chlorofluoroether compounds preferably being those having complementary properties (e.g., providing improved emulsion stability).

In another aspect of this invention, the chlorofluoroether composition is prepared by direct fluorination, i.e., by contacting the corresponding fluorinatable chloroether or chlorofluoroether precursor of the perhalogenated chlorofluoroether compound with fluorine. ("Fluorinatable" means that the precursor contains carbon-bonded hydrogen atoms which are replaceable with fluorine and may contain unsaturation which can be saturated with fluorine.) The resulting perhalogenated chlorofluoroether compound can be made with essentially the same number and spatial arrangement of carbon, oxygen, and chlorine atoms as the precursor thereof. If a chlorofluoroether composition which consists or consists essentially of a selected mixture of perhalogenated chlorofluoroether compounds is desired, a selected mixture of the corresponding precursor compounds can be fluorinated or, alternatively, the selected precursor compounds can be separately fluorinated and then blended.

The direct fluorination of the fluorinatable chloroether or chlorofluoroether precursor can be carried out at temperatures typically used in direct fluorination, e.g., at moderate or near ambient temperatures such as −20° C. to +50° C., using a stoichiometric excess of fluorine gas, which is preferably diluted with an inert gas, such as nitrogen, to minimize or avoid the hazards of pure fluorine gas and to control the amount of heat generated upon contact of the precursor with fluorine. The fluorination is preferably carried out in an oxygen- and water-free environment and can be carried out in the presence of solid, particulate scavenger, e.g., sodium fluoride, for the hydrogen fluoride by-product generated. Liquid phase direct fluorination can be employed and involves using an inert liquid, such as a fluorocarbon or chlorofluorocarbon liquid, as a reaction medium. Both scavenger and an inert liquid reaction medium can be utilized, if desired. The fluorination is preferably carried out by liquid phase direct fluorination in the absence of hydrogen fluoride scavenger by using a temperature and inert gas flow rate sufficient to volatilize hydrogen fluoride by-product and enable its removal from the fluorination zone as it is generated.

In another aspect, this invention provides a fluorochemical composition containing the chlorofluoroether composition hereinbefore described as the sole essential chlorofluoroether component of the fluorochemical composition.

Although direct fluorination is a substitution method involving the replacement of hydrogen atoms with fluorine, direct fluorination provides higher yields and purer products than do other substitution methods such as the electrochemical fluorination and cobalt trifluoride methods. (See, e.g., U.S. Pat. No. 5,093,432 (Bierschenk et al.).) The purity of the chlorofluoroether compositions of the invention is further enhanced by the use of single precursor compounds or selected (rather than random) mixtures thereof, and by the use of primary, rather than secondary, chlorine-containing precursors (i.e., precursors containing chlorine atoms which are bonded only to primary, rather than secondary, carbon atoms). Primary chlorine has less tendency to cleave and migrate to other bonding sites during the fluorination process than does secondary chlorine. (See J. L. Adcock and W. D. Evans, J. Org. Chem. 1984, 49 2719-23.) Mixtures of unpredictable composition are thereby minimized or avoided.

In addition, primary chlorine has been found to be less reactive toward nucleophiles and reducing agents than is secondary chlorine or primary bromine, so the chlorofluoroether compositions of the invention are less likely to be reactive within the human body than are secondary chlorine-containing or primary bromine-containing chlorofluoroether compositions. This characteristic is important, as the chlorofluoroether compositions of the invention are believed to be capable of dissolving and transporting oxygen and are therefore potentially useful in invasive medical applications where reducing and nucleophilic conditions exist. Because of their inertness and purity, the compositions are also useful as cleaners and degreasers, heat transfer agents, e.g., vapor phase soldering fluids and electronic test fluids, solvents, hydraulic fluids, and low temperature lubricants.

Chlorofluoroether compositions of the invention which are suitable for most uses generally contain perhalogenated chlorofluoroether compound(s) which boil at temperatures ranging from about 90° C. to about 300° C., and those suitable for invasive medical use preferably contain compounds which boil at temperatures ranging from about 100° C. to about 200° C., more preferably about 130° C. to about 165° C., as lower boiling compound(s) may tend to exit the body too quickly and higher boiling compound(s) may be retained longer than desired.

A class of normally liquid chlorofluoroether compositions of this invention is that whose members consist or consist essentially of one (or of a selected mixture) of perhalogenated chlorofluoroether compounds which fall within the following representative general formula:

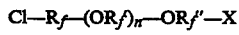

$$Cl-R_f-(OR_f')_n-OR_f''-X \quad I$$

wherein $R_f$ and $R_f''$ are each independently selected from the group consisting of $C_1$ to $C_{12}$, preferably $C_1$ to $C_6$, linear perfluoroalkylene, branched perfluoroalkylene wherein the branch optionally contains 1 or 2 ether oxygen atoms and optionally contains primary chlorine, and unsubstituted, perfluoroalkyl-substituted, perfluoroalkoxy-substituted, or perfluoroalkylene-substituted perfluorocycloalkylene wherein the substituent optionally contains primary chlorine; each $R_f'$ is independently selected from the group consisting of $C_2$ to $C_{12}$, preferably $C_2$ to $C_6$, linear perfluoroalkylene, branched perfluoroalkylene wherein the branch optionally contains 1 or 2 ether oxygen atoms and optionally contains primary chlorine, and unsubstituted, perfluoroalkyl-substituted, perfluoroalkoxy-substituted, or perfluoroalkylene-substituted perfluorocycloalkylene wherein the substituent optionally contains primary chlorine; X is selected from the group consisting of fluorine and primary chlorine; n is an integer of 0 to 4, preferably 0 to 2; and the total number of ether oxygen atoms in the compound can be 1 to 5, the ether oxygen atoms being separated by at least 2 catenary carbon atoms. The total number of carbon atoms in the compound is preferably 5 to 25, more preferably 7 to 10, and the total number of chlorine atoms in the compound is preferably 1 to 4, more preferably 1 to 2. Preferably, $R_f$, each $R_f'$ and $R_f''$ are linear perfluoroalkylene, are independently selected from linear perfluoroalkylene and unsubstituted perfluorocycloalkylene, or are independently selected from linear perfluoroalkylene and branched perfluoroalkylene.

The chlorofluoroether compositions of this invention can be prepared from their hydrogen-containing, saturated or unsaturated chloroether (non-fluorinated) or chlorofluoroether (partially-fluorinated) analogs which are fluorinatable by known fluorination methods such as direct fluorination. (See, e.g., U.S. Pat. Nos. 4,755,567, 4,859,747, and 5,093,432 (Bierschenk et al.) and International Patent Publication No. WO 90/06296 (Minnesota Mining and Manufacturing Company) which disclose direct fluorination techniques useful in the fluorination of ethers.) Although the perhalogenated chlorofluoroether products may contain small amounts of fluorinated materials having one or a few residual hydrogen atoms, the chlorofluoroether compositions of this invention are essentially fully-halogenated, i.e., perhalogenated, with a residual carbon-bonded hydrogen content of generally less than about 0.4 mg/g and preferably less than about 0.1 mg/g, e.g., 0.01 to 0.05 mg/g. This residual hydrogen content can be lowered or essentially completely removed upon treatment with fluorine (or fluorine diluted with inert gas) at elevated temperature, e.g., 150° C. or higher, as a "polishing" finishing step.

In one direct fluorination process (the "solids fluorination technique") used to prepare the chlorofluoroether compositions of this invention, the precursor chloroether or chlorofluoroether starting material is contacted with fluorine diluted with an inert gas, such as helium or, preferably, nitrogen, at low initial concentrations of fluorine of about 5 to 25 volume %, preferably about 10 to 15 volume %, and at low initial temperature, which is preferably −20° C. to 0° C. As the fluorination reaction proceeds, the fluorine concentration can be gradually increased up to 50 volume % or even up to 100 volume %, and the reaction temperature is increased, e.g., to 40° C.-60° C. and such conditions can be maintained until the precursor is perhalogenated. The precursor is fluorinated in the presence of a hydrogen fluoride scavenger, such as potassium fluoride or, preferably, sodium fluoride. The scavenger may be in particulate form such as pellets or, preferably, powder. Generally, sufficient scavenger is utilized such that all of the hydrogen fluoride by-product generated in the fluorination process is scavenged. Scavenger:precursor weight ratios of from about 1:1 to about 20:1 have been found useful. Using this method, the precursor may be mixed with or coated on the scavenger and the mixture fluorinated in a fluorination apparatus such as a stationary metal tube reactor, a rotating drum reactor, or a fluidized bed reactor, this technique generally giving yields of about 15 to 30 mol of the desired compound(s). Typical reaction times to obtain such yields vary from about 24 hours to about 48 hours, depending upon the reactor system utilized.

Another method of fluorination (the "liquid phase fluorination technique") that can be used to make the chlorofluoroether compositions of this invention involves making a very dilute dispersion or, preferably, solution of the precursor(s) in a liquid reaction medium, which is relatively inert to fluorine at the fluorination temperatures used, the concentration of the starting material thus being relatively low so as to more easily control the reaction temperature. The reaction mixture can also contain or have dispersed therein a hydrogen fluoride scavenger such as sodium fluoride, the scavenger:precursor weight ratio being, for example, from about 0.5:1 to 7:1. The reaction mixture can be vigorously agitated while the fluorine gas is bubbled through it, the fluorine preferably being used in admixture with an inert gas, such as nitrogen, at a concentration of about 5 to 50 volume %, more preferably about 10 to 25 volume %, and being maintained in stoichiometric excess throughout the fluorination, e.g., up to 15 to 40%, or higher, depending on the particular starting material and the efficiency of the equipment used, such as the stirrer. Yields generally in the range of about 30–77 mol %, and, with experience, as high as 65 to about 80 mol %, of the perhalogenated product may be achieved by this method.

Suitable liquids useful as reaction media for the liquid phase fluorination technique are chlorofluorocarbons such as Freon TM 113, 1,1,2-trichlorotrifluoroethane, and Freon TM 11, fluorotrichloromethane; chlorofluoroethers such as the chlorofluoroether compositions of this invention; Fluorinert TM electronic liquids FC-75 perfluoroether, FC-72 perfluoroalkane , and FC-40 perfluorotrialkylamine; perfluoroalkanes such as perfluoropentane and perfluorodecalin; perfluoropolyethers; and perfluoroacetals. Mixtures of such liquids can be used, e.g., to get good dispersion of precursor and intermediate reaction products. The reaction media are conveniently used at atmospheric pressure. Lower molecular weight members of the above classes of reaction media can also be used, but elevated pressures are then required to provide a liquid phase.

The liquid phase fluorination reaction is generally carried out at a temperature between about −10° C. to +50° C., preferably between about −10° C. to 0° C. if a hydrogen fluoride scavenger is used, and, if such a scavenger is not used, between about 0° C. to 150° C., preferably about 0° C. to 50° C., most preferably about 10° C. to 30° C., the temperature being sufficient to volatilize the hydrogen fluoride by-product and, with the aid of the inert gas, flowing at a sufficient rate, cause the purging of the by-product from the fluorination reactor as it is generated. At these temperatures, the liquids utilized as reaction media do not react appreciably with the diluted fluorine and are essentially inert. The reaction medium and other organic substances may to some extent be present in the gaseous reactor effluent, and a condenser may be used to condense the gaseous reaction medium and such substances in the effluent and permit the condensate to return to the reactor. The condenser should be operated so as to minimize or prevent the return to the reactor of hydrogen fluoride by-product (which could have an adverse effect on yield of product if allowed to remain in the reactor during fluorination). The return of the hydrogen fluoride can be minimized or prevented by selective condensation of the organic materials while allowing the hydrogen fluoride to pass through the condenser, or by total condensation of both hydrogen fluoride and the organic materials into a separate vessel followed, if desired, by separation of the hydrogen fluoride as the upper liquid phase and the return of the lower liquid phase.

The liquid phase fluorination reaction may be carried out in a batch mode, in which all of the precursor is added to the liquid prior to fluorination to provide a precursor concentration of up to about 10% by weight, and the fluorine-containing gas is then bubbled through the precursor-containing liquid. The reaction can also be carried out in a semi-continuous mode, in which the precursor is continuously pumped or otherwise fed neat, or as a diluted solution or dispersion in a suitable liquid of the type used as a reaction medium, into the reactor, e.g., at a rate of about 1 to 3 g/hr into 400 mL of liquid reaction mixture, as fluorine is bubbled through, e.g., at a fluorine flow rate of about 40 to 120 mL/min and an inert gas flow rate of about 150 to 600 Ml/min. The fluorination can also be carried out in a continuous manner, in which the precursor (either neat or dissolved or dispersed in a suitable liquid of the type used as a reaction medium) is continuously pumped or otherwise fed into the reactor containing the reaction medium as the fluorine-containing gas is introduced, as described above, and the stream of unreacted fluorine, hydrogen fluoride gas, and inert carrier gas is continuously removed from the reactor, as is a stream of liquid comprising perhalogenated product, incompletely halogenated precursor, and inert liquid reaction medium, and the necessary separations are made to recover the chlorofluoroether composition. If desired, the unreacted fluorine and the incompletely fluorinated precursor can be recycled. The amount of inert liquid medium in the reactor can be maintained at a constant level by addition of recycled or fresh liquid. The product from the batch mode generally will have significant residual hydrogen, e.g., about 7 mg/g, whereas the product made by the continuous or semicontinuous mode will generally have less residual hydrogen, e.g., less than 0.1 mg/g. In general, the continuous addition of precursor is preferred and provides a higher yield, better product quality, and more efficient use of fluorine, though the batch mode has similar advantages if the "polishing" finishing step is used.

Due to the extremely high exothermicity of the fluorination reaction, a cooled liquid or ice bath is generally employed in order that acceptable rates of reaction may be achieved. When the reaction is complete, the reactor is purged of fluorine and the reactor contents are removed. In the solids fluorination technique, the reactor contents can be mixed with Freon TM 113 or Fluorinert TM FC-72 solvent, the resulting slurry filtered, and the solvent stripped, e.g., by vacuum distillation, to provide crude product. Where the fluorination is carried out by the liquid phase fluorination technique in the presence of a hydrogen fluoride scavenger, the spent scavenger can be separated by filtration or decantation from the liquid reactor contents and the latter then distilled to separate the reaction medium from the crude product. Where the fluorination is carried out by the liquid phase fluorination technique without using the scavenger, the reaction product mixture can be distilled to recover the product.

The crude product can be treated with a base, e.g., sodium hydroxide, or with fluorine (by the polishing finishing technique) to remove hydride impurities, and the so-treated product can then be distilled. The order of these purification steps can be varied to obtain best results.

Precursor chloroethers used to prepare the chlorofluoroether compositions of the invention can be prepared in a variety of ways using standard methods. For example, the chloroethers can be prepared by reaction of ether oxygen-containing alcohol(s) (or an ether such as tetrahydrofuran) with chlorine-containing reagents such as thionyl chloride, phosphorus pentachloride, or phosphorus oxychloride. The precursor chloroethers can also be prepared by reaction of alcohol(s) with β,ω-dichloroalkanes or α,ω-bromochloroalkanes under basic conditions, or by reaction of metal, e.g., silver, salts of ether acids with chlorine. (Note that as an alternative route to a perhalogenated chlorofluoroether, an ether acid derivative can be directly fluorinated to form a perfluorinated ether acid, a metal salt of which can then be prepared and decarboxylated in the presence of a chlorinating agent to give the perhalogenated chlorofluoroether (see M. Hudlicky, *Chemistry of Organic Fluorine Compounds*, Second Edition, pages 225–26, Ellis Horwood, New York (1992)).)

If desired, chlorofluoroether, i.e., partially-fluorinated, precursors can be utilized to prepare the chlorofluoroether compositions of the invention, and these precursors can be prepared from reactive fluorochemical intermediates which can be obtained through known fluorination techniques. For example, certain partially-fluorinated precursors can be prepared by addition of alcohol(s) to chlorotrifluoroethylene (as referenced in Hudlicky, supra, page 409), and partially-fluorinated ether oxygen-containing alcohols and partially-fluorinated alcohols can be utilized in the reactions described above for the preparation of chloroether precursors.

Useful precursor chloroethers and chlorofluoroethers for conversion by direct fluorination to the perhalogenated chlorofluoroethers of the chlorofluoroether compositions of the invention include the following compounds and selected mixtures thereof:

$C_8H_{17}OCH_2Cl$
$C_4H_9(OC_2H_4)_2OCH_2Cl$
$C_8H_{17}OC_2H_4Cl$
$C_7H_{15}OC_2H_4Cl$
$C_5H_{11}(OC_2H_4)_2Cl$
$C_6H_{13}(OC_2H_4)_2Cl$
$C_4H_9(OC_2H_4)_2Cl$
$C_3H_7(OC_2H_4)_3Cl$

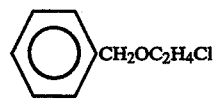

$C_6H_{13}O(CH_2)_3Cl$
$C_4H_9OC_2H_4O(CH_2)_3Cl$
$C_2H_5(OC_2H_4)_2O(CH_2)_3Cl$
$C_5H_{11}O(CH_2)_4Cl$
$C_4H_9O(CH_2)_5Cl$
$C_3H_7O(CH_2)_6Cl$
$C_2H_5O(CH_2)_7Cl$
$CH_3O(CH_2)_8Cl$

-continued

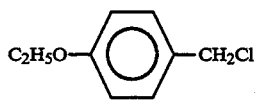

$C_4H_9OCH_2C(CH_3)_2CH_2Cl$

$C_5H_{11}OCH_2CHCH_2Cl$ (with CH$_3$ branch)

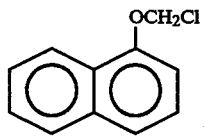

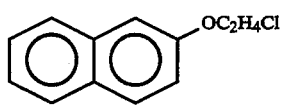
$C_3H_7OCH$ (with CH$_2$CH$_2$Cl groups)

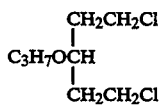
$C_5H_{11}OCH$ (with CH$_2$Cl groups)

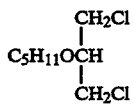

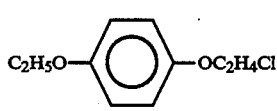
$C_4H_9OCHCH_2OC_2H_4Cl$ (with CH$_3$)

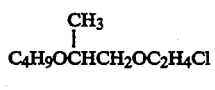
$C_3H_7OCHCH_2OC_2H_4Cl$ (with CH$_3$)

$ClCH_2O(CH_2)_7Cl$
$Cl(CH_2)_2O(CH_2)_6Cl$
$Cl(CH_2)_3O(CH_2)_5Cl$
$Cl(CH_2)_4O(CH_2)_4Cl$

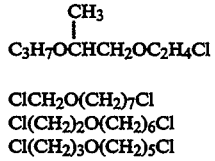

$ClCH_2C(CH_3)_2CH_2O(CH_2)_3Cl$
$ClCH_2O(CH_2)_6OCH_2Cl$
$ClC_2H_4O(CH_2)_4OC_2H_4Cl$
$ClC_2H_4O(CH_2)_3O(CH_2)_3Cl$
$Cl(CH_2)_3O(CH_2)_2O(CH_2)_3Cl$

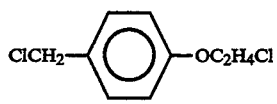

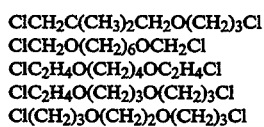

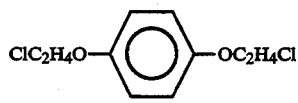

-continued

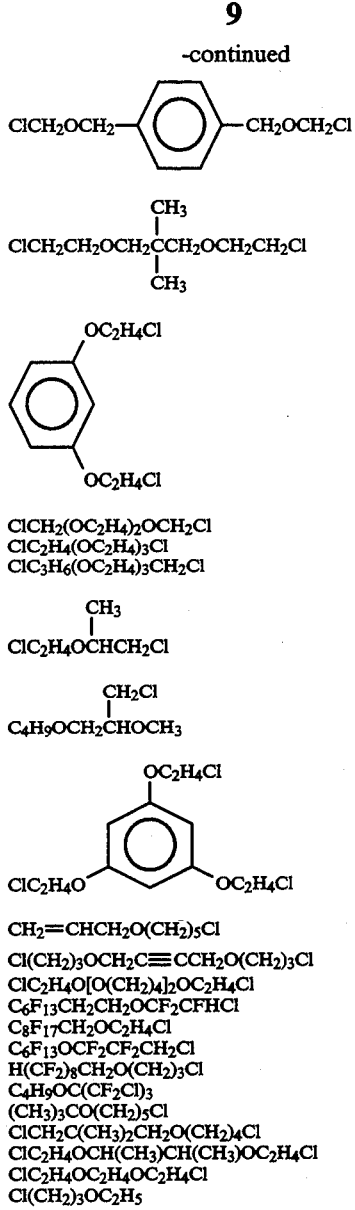

ClCH2(OC2H4)2OCH2Cl
ClC2H4(OC2H4)3Cl
ClC3H6(OC2H4)3CH2Cl

ClC2H4OCHCH2Cl
         |
         CH3

C4H9OCH2CHOCH3
         |
         CH2Cl

CH2=CHCH2O(CH2)5Cl
Cl(CH2)3OCH2C≡CCH2O(CH2)3Cl
ClC2H4O[O(CH2)4]2OC2H4Cl
C6F13CH2CH2OCF2CFHCl
C8F17CH2OC2H4Cl
C6F13OCF2CF2CH2Cl
H(CF2)8CH2O(CH2)3Cl
C4H9OC(CF2Cl)3
(CH3)3CO(CH2)5Cl
ClCH2C(CH3)2CH2O(CH2)4Cl
ClC2H4OCH(CH3)CH(CH3)OC2H4Cl
ClC2H4OC2H4OC2H4Cl
Cl(CH2)3OC2H5

Representative examples of the perhalogenated chlorofluoroethers of the chlorofluoroether compositions of this invention include the perfluorinated (i.e., having essentially all hydrogens replaced with fluorine) counterparts of the precursor chloroethers and chlorofluoroethers listed above. Where the precursors have unsaturation, the corresponding perhalogenated chlorofluoroethers are saturated.

The chlorofluoroether compositions of the invention are useful as cleaners, degreasers, heat transfer agents, e.g., vapor phase soldering fluids and electronic test fluids, solvents, hydraulic fluids, and low temperature lubricants. The compositions are also believed to be capable of dissolving and transporting oxygen and are therefore potentially useful as blood substitutes which can be employed invasively in the treatment of vascular obstructions, as adjuvants to cancer radiation treatment or chemotherapy, and as imaging contrast agents. For such uses, emulsions of the compositions can be prepared by methods such as those described in, e.g., U.S. Pat. Nos. 3,911,138 (Clark) and U.S. Pat. No. 5,077,036 (Long), which descriptions are incorporated herein by reference. Minor amounts of optional components, e.g., surfactants, may be added to the chlorofluoroether compositions to impart particular desired properties for particular uses.

This invention is further illustrated by the following examples, but the particular materials and amounts thereof recited in these examples, as well as other conditions and details, should not be construed to unduly limit this invention.

EXAMPLES

Example 1

Preparation of Perfluoro-4,4'-dichlorobutyl Ether
(Cl—C4F8—O—C4F8—Cl)

The precursor 4,4'-dichlorobutyl ether was prepared from tetrahydrofuran by reaction with phosphorus oxychloride (POCl3). A 1-L round-bottomed flask was equipped with a stirrer, thermometer, reflux condenser, and a dropping funnel. The flask was charged with 50 g of concentrated sulfuric acid and heated to 95°–105° C. with stirring. A mixture of 30 mL of POCl3 in 80 mL of tetrahydrofuran was slowly added to the flask while maintaining the temperature. After addition of the mixture was complete, the resulting mixture was maintained at this temperature for an additional half hour with stirring. Then, approximately 350 mL of water was added to quench the reaction, while continuing the stirring and temperature maintenance. The contents of the flask were transferred to a separatory funnel and extracted with methylene chloride. The extracts were then distilled under reduced pressure to yield the desired 4,4'-dichlorobutyl ether.

A two-liter metal reactor equipped with an internal stirrer, gas inlet, thermometer, organic feed tube, cooling jacket, and low temperature condenser was charged with 1.8 L of Freon TM 113 and purged with nitrogen. The reactor was maintained at about 18.5° C. The gas stream was changed to a mixture of 240 mL/min of fluorine and 1200 mL/min of nitrogen, and a solution of 100 g of 4,4'-dichlorobutyl ether precursor diluted to 260 mL with Freon TM 113 was added to the reactor at a rate of 13 mL/hour. The total addition time was 20 hours. After purging the reactor with nitrogen gas to remove fluorine, the contents were removed from the reactor, and the Freon TM 113 separated by distillation, leaving a 235 g residue. The residue was heated with a caustic solution, and the product was then further purified by distillation using a 6" Vigreux column (to a main cut of 184 g, boiling point 146°–8° C.). The structure of the product was confirmed by $^{19}F$ NMR and GC/MS.

Example 2

Preparation of
Perfluoro-1,11-dichloro-3,6,9-trioxaundecane
(Cl—(C2F4O)3—C2F4—Cl)

The precursor Cl-(C2H4O)3—C2H4—Cl was prepared by treatment of tetraethylene glycol with thionyl chloride. 388.4 g of tetraethylene glycol was added dropwise to a flask containing 850 mL of thionyl chloride, with stirring. After addition was complete, the resulting solution was heated to 100° C. for several hours, until gas evolution was no longer observed. The excess thionyl chloride was then removed by distillation, the residue was washed with water, and the residue was then distilled to yield the desired Cl—(C2H4O)3—C2H4—Cl precursor.

This precursor was fluorinated, treated with base, and distilled in essentially the same manner as in Example 1 to yield 122.6 g of Cl—($C_2F_4O$)$_3$—$C_2F_4$—Cl (boiling point 137° C.).

Example 3

Preparation of Perfluoro-1-chloro-3,6-dioxadecane ($C_4F_9$—O—$C_2F_4$—O—$C_2F_4$—Cl)

The precursor $C_4H_9$—O—$C_2H_4$—O—$C_2H_4$—Cl was prepared by treatment of butoxyethoxy ethanol (butyl carbitol) with thionyl chloride. 145 g of thionyl chloride was added dropwise to a flask containing 179 g of butyl carbitol and 2 mL of dimethyl formamide, with stirring. After addition was complete, the resulting solution was stirred overnight at room temperature. The excess thionyl chloride was then removed on a rotary evaporator, and the residue was poured into water. The resulting homogeneous solution was extracted with an equal volume of ether, and the ether extracts were washed with dilute (approximately 5% by weight) KOH solution. The washed ether extracts were then dried, the ether was removed using rotary evaporation, and the residue was distilled with an 8" Vigreux column to yield $C_4H_9$—O—$C_2H_4$—O—$C_2H_4$—Cl (boiling point 61°-66° C. @0.15 torr).

The $C_4H_9$—O—$C_2H_4$—O—$C_2H_4$—Cl precursor was fluorinated, treated with base, and distilled in essentially the same manner as in Example 1. The boiling point of the resulting compound, $C_4F_9$—O—$C_2F_4$—O—$C_2F_4$—Cl, was 114°-116° C.. The structure of the product was confirmed by GC/MS, IR, and $^{19}F$ NMR.

Example 4

Preparation of Perfluoro-1-chloro-3-oxanonane ($C_6F_{13}$—O—$C_2F_4$—Cl)

The precursor $C_6H_{13}OCF_2CHFCl$ was prepared by the base-catalyzed addition of n-hexanol to chlorotrifluoroethylene (CTFE). A 1-L round-bottomed flask was fitted with a stirrer, a dry ice condenser, and a gas inlet. The flask was charged with 102 g of n-hexanol, 3.93 g of powdered KOH, and 250 mL of THF, and the flask contents were heated to 55°-60° C. CTFE was then added to the flask through the gas inlet, resulting in an exotherm. After the exotherm, an additional 2.4 g of KOH was added to the flask, followed by slow addition of CTFE. After the resulting exotherm had subsided, the flask contents were filtered to remove white precipitate, and then an additional 6.3 g of KOH was added to the filtrate, followed again by addition of CTFE. A total of 120 g CTFE was used. GLC indicated a 1:4 mixture of unreacted hexanol and the desired product, $C_6H_{13}$—O—$CF_2CHFCl$. The mixture was quenched with ~1 L of water, extracted twice with methylene chloride, and then was dried and distilled to yield a crude product mixture of unreacted n-hexanol and the desired product, $C_6H_{13}$—O—$CF_2CHFCl$.

The crude product mixture was treated with excess acetyl chloride to convert the unreacted n-hexanol to n-hexyl acetate. The resulting mixture, containing $C_6H_{13}$—O—$CF_2CHFCl$ and n-hexyl acetate, was then fluorinated (essentially as in Example 1) and distilled. The resulting crude $C_6F_{13}$—O—$C_2F_4$—Cl was then treated with base and distilled (boiling point 29° C. at 0.15 torr) essentially as in Example 1. The structure of the product was confirmed by GC/MS.

Example 5

Preparation of Perfluoro-1-chloro-3,6-dioxadodecane ($C_6F_{13}$—O—$C_2F_4$—O—$C_2F_4$—Cl)

The precursor $C_6H_{13}OC_2H_4OC_2H_4Cl$ was prepared by treatment of hexyloxyethoxyethanol (hexyl carbitol) with thionyl chloride. 130.9 g of thionyl chloride was added dropwise to a flask containing 190 g of butyl carbitol and 2 mL of dimethyl formamide, with stirring. After the addition was complete, the resulting solution was heated at reflux for two hours. Excess thionyl chloride was removed under aspirator pressure. The remaining residue was dissolved in ~250 mL of Freon TM 113 and washed with water. The Freon TM was removed under aspirator pressure, and the washed residue was distilled to yield the desired product (boiling point 95°-100° C. @0.9 torr).

The $C_6H_{13}OC_2H_4OC_2H_4Cl$ precursor was fluorinated, treated with base, and distilled essentially as in Example 1 to yield 206.5 g of product, $C_6F_{13}$—O—$C_2F_4$—O—$C_2F_4$—Cl (boiling point 146°-148° C.). The structure of the product was confirmed by $^{19}F$ NMR, IR, and GC/MS.

Example 6

Preparation of Perfluoro-1,10-dichloro-3,8-dioxadecane (Cl—$C_2F_4$—O—($CF_2$)$_4$—$OC_2F_4$—Cl)

34.8 g of technical grade (85%) HO—$C_2H_4$—O—$CH_2$—C≡C—$CH_2$—O—$C_2H_4$—OH was reduced using 0.4 g of 10% Pd/C catalyst in methanol. The mixture was filtered to remove the catalyst, and the methanol was removed under aspirator pressure to yield 34.9 g of crude diol, HO—$C_2H_4$—O—($CH_2$)$_4$—O—$C_2H_4$—OH. This was dissolved in about 50 mL methylene chloride, and this solution was added dropwise to 40 mL thionyl chloride with heating and stirring. Upon complete addition of the solution, the resulting mixture was heated at about 50° C. for 8 hours. Distillation of the mixture gave a main fraction of 20.9 g, boiling point 95° C. @0.6 torr. This fraction was identified as being predominantly Cl—$C_2H_4$—O—($CH_2$)$_4$—O—$C_2H_4$—Cl by GC/MS. This procedure was repeated in essentially the same manner but on a larger scale to produce sufficient material for the subsequent fluorination.

100g of Cl—$C_2H_4$—O—($CH_2$)$_4$—O—$C_2H_4$—Cl was fluorinated in essentially the same manner as in Example 1. The Freon TM 113 solvent was then distilled to yield 222 g of crude product, which was treated with base and then azeotropically distilled to yield a 140.2 g fraction. This fraction was washed with water, dried over MgSO$_4$, and distilled to a main fraction boiling at 140°-2° C. $^{19}F$ NMR analysis of this main fraction showed it to be >95% the desired Cl—$C_2F_4$—O—($CF_2$)$_4$—$OC_2F_4$—Cl product. The isomeric purity of the product was 99.5%.

Comparative Example 1

9.0 g of a starting mixture of chloro-isomers of Cl—$C_4F_8$—O—$C_4F_8$—Cl, 2.0g of powdered NaOH, and 40 mL of tetraglyme was stirred at reflux for 20 hours. The resulting isomeric product mixture was recovered by addition of 500 mL of water followed by separation of the lower fluorochemical phase, and the isomer distribution was determined by $^{19}F$ NMR. The distributions of isomers in the starting mixture and in the resulting product mixture are shown in Table 1 below.

TABLE 1

| Structure | Starting Mixture | Product Mixture |
|---|---|---|
| Cl—C$_4$F$_8$—O—CF$_2$CF$_2$CF$_2$CF$_2$—Cl | 93.7% | 97.5% |
| Cl—C$_4$F$_8$—O—CF$_2$CF$_2$CF(Cl)—CF$_3$ | 3.9% | 0% |

These data demonstrates that the secondary chloride was more reactive toward the NaOH nucleophile than was the primary chloride.

Comparative Example 2

A mixture of 9.0 g of n—C$_8$F$_{17}$—Br, 1.0 g of (C$_4$F$_9$OC$_2$F$_4$O)$_2$CF$_2$, 0.19 g of 18-crown-6 ether, 2.0 g of powdered NaOH, and 20 mL of tetraglyme was heated at reflux for 29 hours. After cooling, dilute sulfuric acid (about 5% by weight) was added to the mixture, resulting in phase separation of the mixture. The lower fluorochemical phase of the phase-separated mixture was isolated by draining. $^{19}$F NMR analysis of the isolated phase revealed 92% n—C$_8$F$_{17}$H and 8% (C$_4$F$_9$OC$_2$F$_4$O)$_2$CF$_2$, demonstrating that the primary bromide was more reactive toward the NaOH nucleophile than the primary chloride of Comparative Example 1 under similar conditions.

Various modifications and alterations of this invention will become apparent to those skilled in the art without departing from the scope and spirit of this invention.

What is claimed is:

1. A chlorofluoroether composition which consists of a perhalogenated chlorofluoroether compound having 8 carbon atoms and at least two primary carbon atoms, 1 ether oxygen atom and two chlorine atoms, each chlorine atom being bonded to a primary carbon atom.

2. The composition of claim 1 wherein said compound is perfluoro-4,4'-dichlorobutyl ether.

3. A compound of claim 1 having the formula:

C$_8$F$_{18}$Cl$_2$O.

4. A compound of claim 1 produced by fluorination of the following precursor compounds selected from the group consisting of:

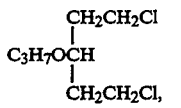

CH$_2$CH$_2$Cl
|
C$_3$H$_7$OCH
|
CH$_2$CH$_2$Cl,

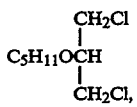

CH$_2$Cl
|
C$_5$H$_{11}$OCH
|
CH$_2$Cl,

ClCH$_2$O(CH$_2$)$_7$Cl,
Cl(CH$_2$)$_2$O(CH$_2$)$_6$Cl,
Cl(CH$_2$)$_3$O(CH$_2$)$_5$Cl,
Cl(CH$_2$)$_4$O(CH$_2$)$_4$Cl, and
ClCH$_2$C(CH$_3$)$_2$CH$_2$O(CH$_2$)$_3$Cl.

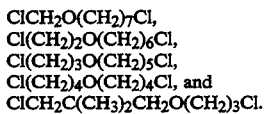

5. A compound having the formula of claim 1 selected from the group consisting of:

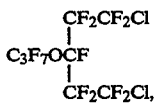

CF$_2$CF$_2$Cl
|
C$_3$F$_7$OCF
|
CF$_2$CF$_2$Cl,

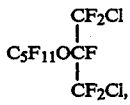

CF$_2$Cl
|
C$_5$F$_{11}$OCF
|
CF$_2$Cl,

ClCF$_2$O(CF$_2$)$_7$Cl,
Cl(CF$_2$)$_2$O(CF$_2$)$_6$Cl,
Cl(CF$_2$)$_3$O(CF$_2$)$_5$Cl,
Cl(CF$_2$)$_4$O(CF$_2$)$_4$Cl, and
ClCF$_2$C(CF$_3$)$_2$CF$_2$O(CF$_2$)$_3$Cl.

* * * * *

UNITED STATES PATENT AND TRADEMARK OFFICE
CERTIFICATE OF CORRECTION

PATENT NO. : 5,420,359
DATED : May 30, 1995
INVENTOR(S) : Goege G. I. Moore

It is certified that error appears in the above-indentified patent and that said Letters Patent is hereby corrected as shown below:

Col. 5 Line 3 "15 to 30 mol of" should be --15 to 30 mol % of--

Col. 7 Line 18 "$\beta,\omega$-dichloroalkanes" should be --$\alpha,\omega$-dichloroalkanes--

Col. 12 Line 30 "C=C" should be --C≡C

Col. 14 Line 3 "$C_8F_{18}$" should be --$C_8F_{16}$--

Signed and Sealed this

Tenth Day of October, 1995

Attest:

BRUCE LEHMAN

Attesting Officer

Commissioner of Patents and Trademarks